(12) United States Patent
Basilion et al.

(10) Patent No.: US 10,207,005 B2
(45) Date of Patent: Feb. 19, 2019

(54) PHOTODYNAMIC THERAPY COMPOSITION

(71) Applicant: CASE WESTERN RESERVE UNIVERITY, Cleveland, OH (US)

(72) Inventors: James Basilion, Cleveland, OH (US); Xinning Wang, Cleveland, OH (US); Clemens Burda, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/629,281

(22) Filed: Jun. 21, 2017

(65) Prior Publication Data

US 2017/0281789 A1   Oct. 5, 2017

Related U.S. Application Data

(63) Continuation-in-part of application No. 14/767,984, filed as application No. PCT/US2014/016932 on Feb. 18, 2014, now Pat. No. 9,889,199.

(60) Provisional application No. 61/765,346, filed on Feb. 15, 2013.

(51) Int. Cl.

| | |
|---|---|
| *A61K 49/00* | (2006.01) |
| *C09B 47/22* | (2006.01) |
| *A61K 31/695* | (2006.01) |
| *A61K 41/00* | (2006.01) |
| *A61K 9/00* | (2006.01) |
| *A61K 47/48* | (2006.01) |
| *A61K 47/64* | (2017.01) |

(52) U.S. Cl.
CPC ...... *A61K 47/48246* (2013.01); *A61K 31/695* (2013.01); *A61K 41/0071* (2013.01); *A61K 47/645* (2017.08); *A61K 49/0036* (2013.01); *A61K 49/0056* (2013.01)

(58) Field of Classification Search
CPC .......... A61K 47/48246; A61K 41/0071; A61K 49/0052; A61K 9/0019; A61K 31/695
USPC ....................................................... 514/630
See application file for complete search history.

(56) References Cited

U.S. PATENT DOCUMENTS

| | | |
|---|---|---|
| 2008/0193381 A1 | 8/2008 | Babich et al. |
| 2009/0061010 A1 | 3/2009 | Zale et al. |
| 2010/0324008 A1 | 12/2010 | Low |
| 2012/0323164 A1* | 12/2012 | Kenney .............. A61K 41/0071 604/20 |

FOREIGN PATENT DOCUMENTS

| | | |
|---|---|---|
| WO | 2008057437 A1 | 5/2008 |
| WO | 2011106639 A1 | 9/2011 |
| WO | 2012106713 A2 | 8/2012 |

OTHER PUBLICATIONS

Extended Search Report for Application No. 14751113.3-1453/2958596, dated Oct. 10, 2016.

Kularatne, Sumith A., et al., "Synthesis and Biological Analysis of Prostate-Specific Membrane Antigen-Targeted Anticancer Prodrugs", Journal of Medicinal Chemistry, vol. 53, No. 21, Nov. 11, 2010, pp. 7767-7777, XP055103918.

Ikeda, Masato, et al., "Supramolecular hydrogel capsule showing prostate specific antigen-responsive function for sensing and targeting prostate cancer cells", Chem. Sci., 2010, 1, 491-498.

* cited by examiner

*Primary Examiner* — Yong L Chu
(74) *Attorney, Agent, or Firm* — Tarolli, Sundheim, Covell & Tummino LLP

(57) ABSTRACT

A phthalocyanine compound or targeted conjugate thereof having the formula (I).

29 Claims, 8 Drawing Sheets

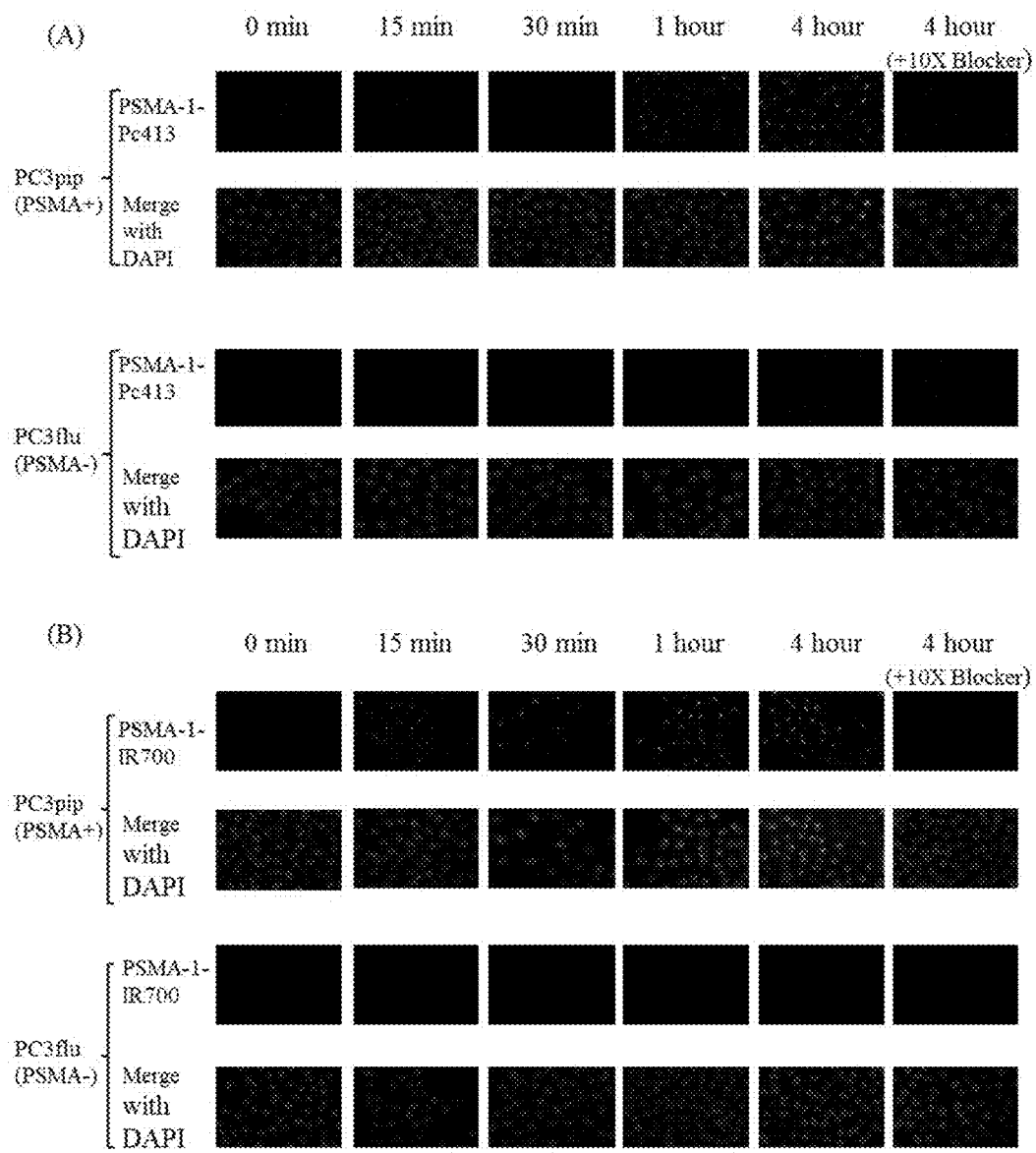
Figs. 5A-B

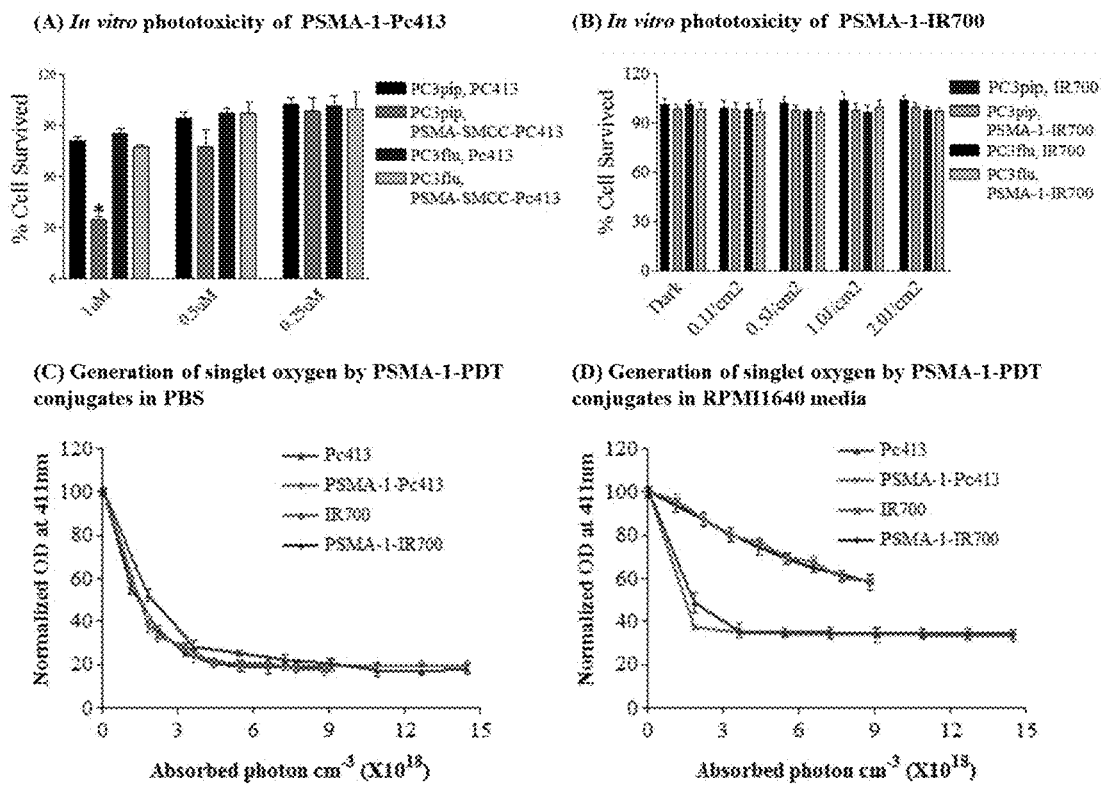
Figs. 6A-D

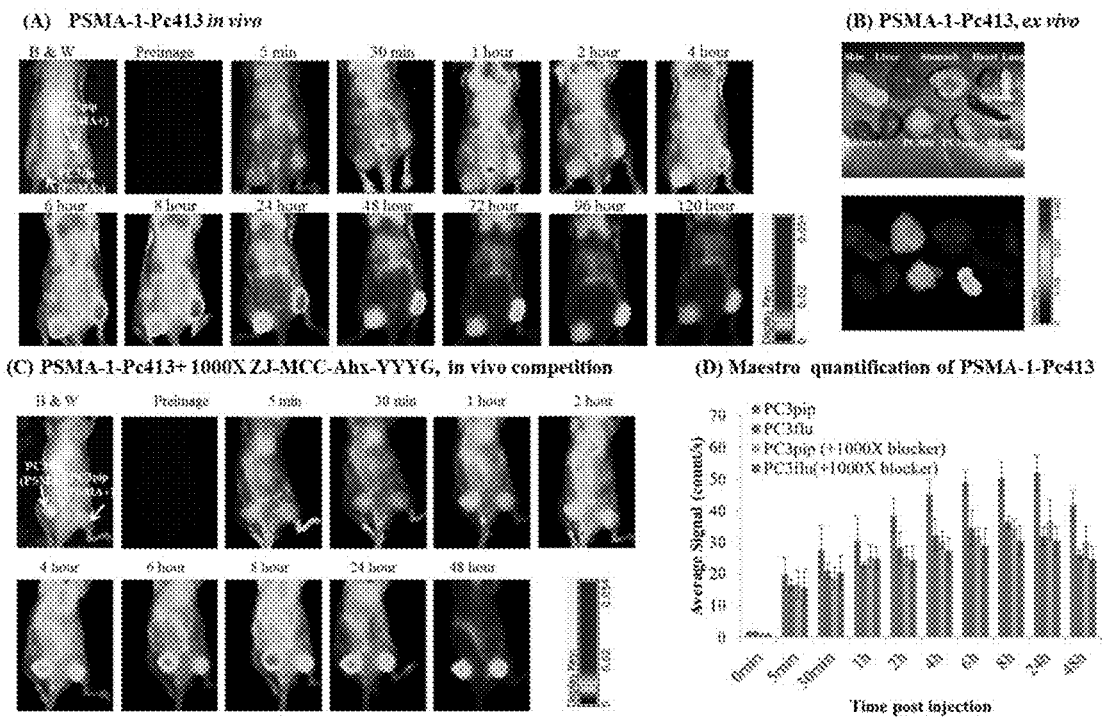
Figs. 7A-D

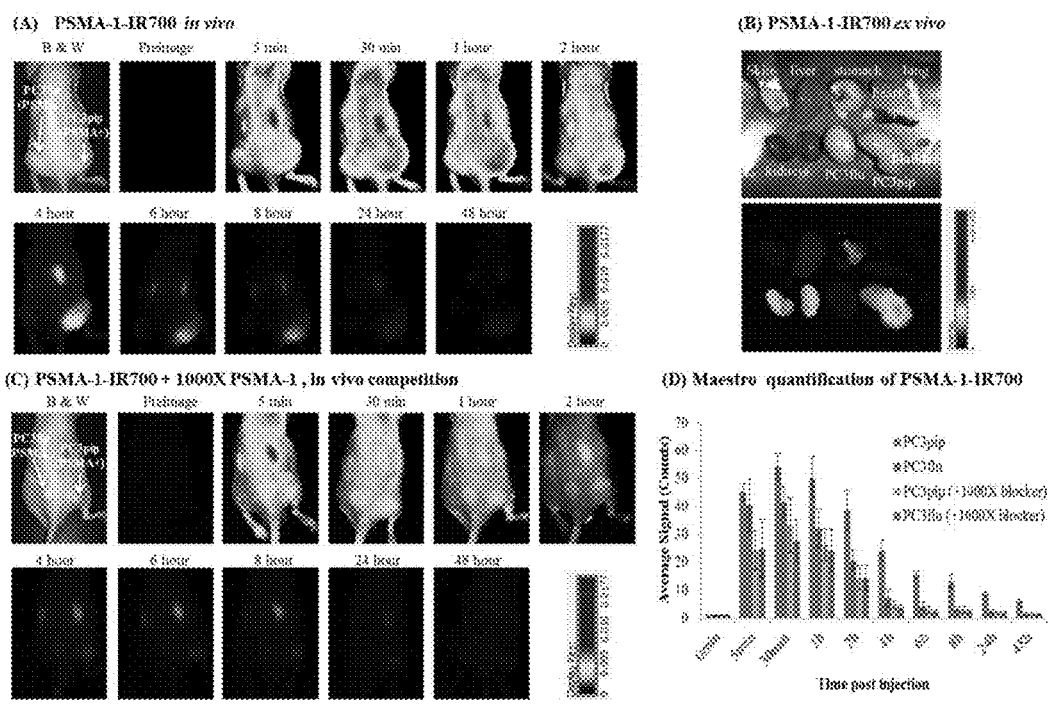
Figs. 8A-D

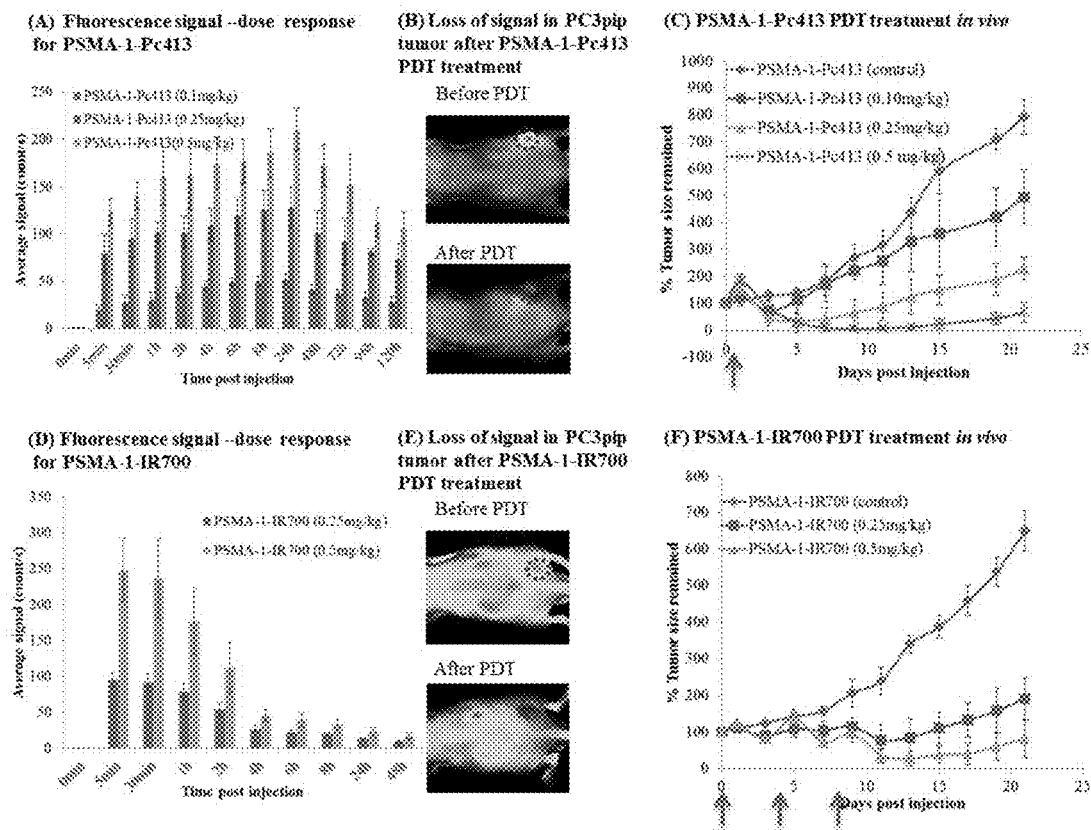
Figs. 9A-F (A) PC3pip tumor
(0.5mg/kg PSMA-1-Pc413)
(no light irradiation)
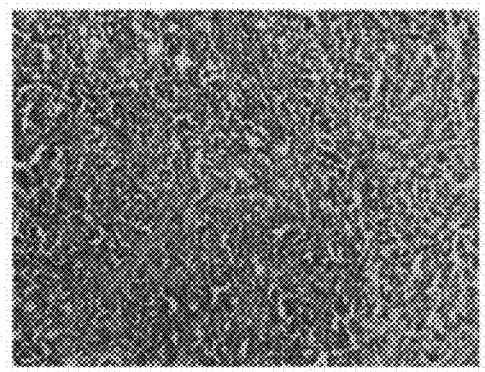
(B) PC3pip tumor
(0.5mg/kg PSMA-1-Pc413)
(150J/cm$^2$ radiant exposure)
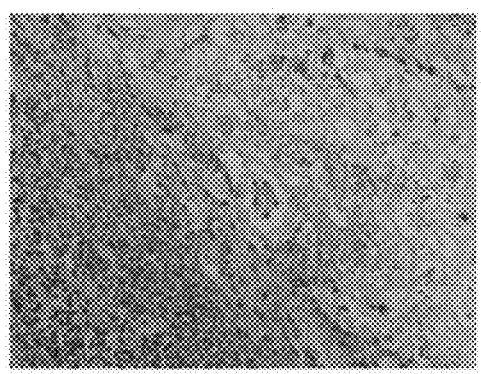
(C) PC3pip tumor
(0.5mg/kg PSMA-1-IR700)
(no light irradiation)
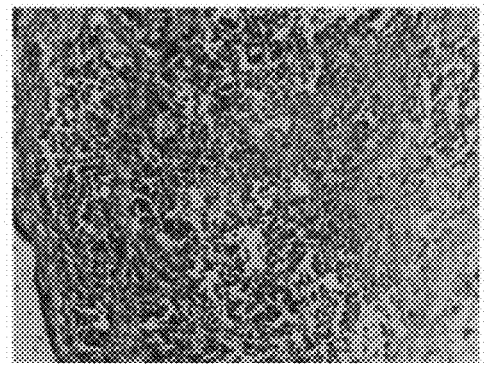
(D) PC3pip tumor
(0.5mg/kg PSMA-1-IR700)
(50J/cm$^2$ radiant exposure)
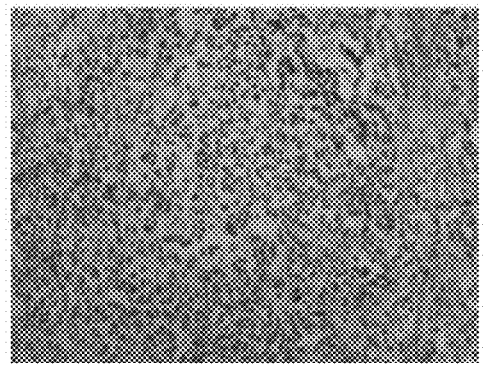
Figs. 10A-D

PHOTODYNAMIC THERAPY COMPOSITION

RELATED APPLICATION

This application is a Continuation-in-Part of U.S. patent application Ser. No. 14/767,984, filed Aug. 14, 2015, which is a National Phase filing of PCT/US2014/016932, Filed Feb. 18, 2014, and claims priority from U.S. Provisional Application No. 61/765,346, filed Feb. 15, 2013, the subject matter of which are incorporated herein by reference in their entirety.

GOVERNMENT FUNDING

This invention was made with government support under Grant No. R01EB12099, awarded by The National Institutes of Health. The United States government has certain rights in the invention.

TECHNICAL FIELD

This application relates to diagnostic and therapeutic compositions, and more particularly relates to compounds for use in photodynamic therapy.

BACKGROUND

Photodynamic therapy, hereinafter also referred to as "PDT", is a process for treating cancer wherein visible light is used to activate a substance, such as a dye or drug, which then attacks the tumor tissue through one or more photochemical reactions, thereby producing a cell-killing, or cytotoxic, effect. When certain photosensitizer compounds are applied to a human or animal body, they are selectively retained by cancerous tissue while being eliminated by healthy tissue. The tumor or cancerous tissue containing the photosensitizer can then be exposed to therapeutic light of an appropriate wavelength and at a specific intensity for activation. The light energy and the photosensitizer cause a photochemical reaction which kills the cells in which the photosensitizer resides.

Phthalocyanines, hereinafter also abbreviated as "Pcs", are a group of photosensitizer compounds having the phthalocyanine ring system. Phthalocyanines are azaporphyrins consisting of four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy is described in International Publication WO 2005/099689. Phthalocyanines strongly absorb clinically useful red or near IR radiation with absorption peaks falling between about 600 and 810 nm, which potentially allows deep tissue penetration by the light.

SUMMARY

Embodiments described herein relate to phthalocyanine compounds and targeted conjugates thereof for use in diagnostic, therapeutic, and theranostic applications and particularly for use in photodynamic therapy (PDT). The phthalocyanine compounds described herein are analogs of the PDT photosensitizing compound Pc4 and have been found to be effective in targeted bioimaging and/or PDT of cancer in a subject.

In some embodiments, the phthalocyanine compound or targeted conjugate thereof can have the formula (I):

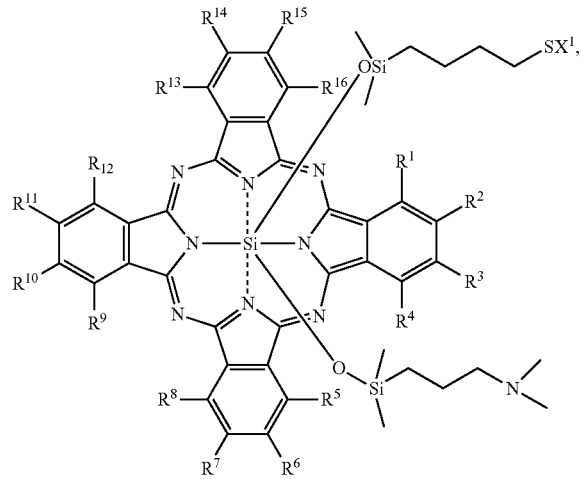

wherein $X^1$ is hydrogen or includes a targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;
$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In other embodiments, the phthalocyanine compound or targeted conjugate thereof can have the formula (II):

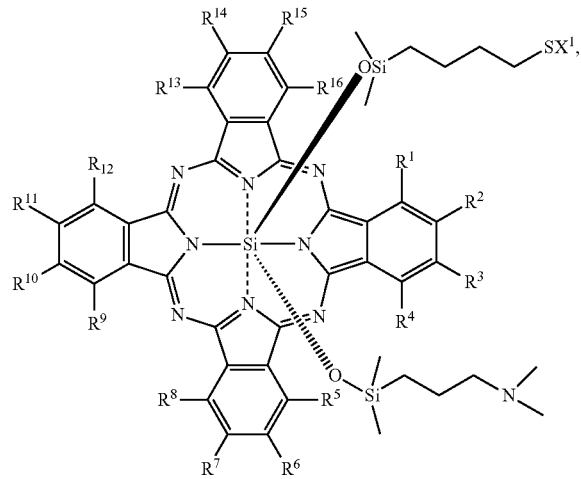

wherein $X^1$ is hydrogen or includes a targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In still other embodiments, the phthalocyanine compound or targeted conjugate thereof can have the formula (III):

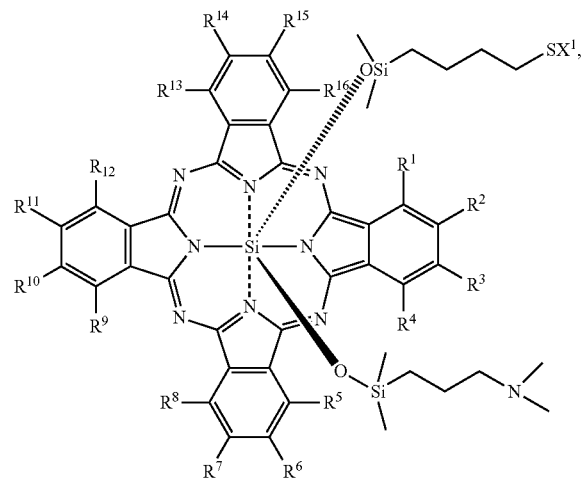

wherein $X^1$ is hydrogen or includes targeting a moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In certain embodiments, the phthalocyanine compound has the formula (IV):

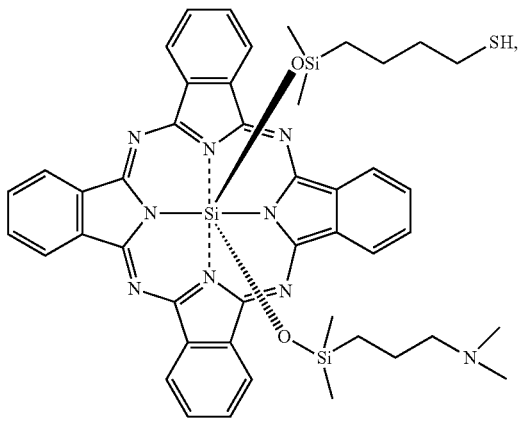

or pharmaceutically acceptable salt thereof.

The phthalocyanine compound can be directly or indirectly coupled or conjugated to the targeting moiety or targeted conjugate thereof. The targeting moiety can be selected from the group consisting of a polypeptide, polynucleotide, small molecule, elemental compound, antibody, and antibody fragments. In some embodiments, the targeting moiety is indirectly linked to the thiol group of the phthalocyanine compound using a linking group. In other embodiments, the targeting moiety is directly linked to the phthalocyanine compound.

In some embodiments, the targeting moiety can include a pyridine-2-ylmethylamino acetic acid (PAMA) ligand, such as a PSMA-1 ligand.

Other embodiments described herein relate to a pharmaceutical composition that includes a phthalocyanine compound or targeted conjugate thereof having the formula (I):

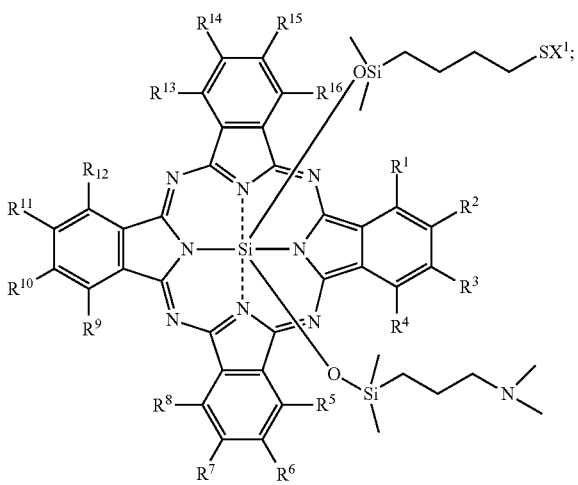

wherein $X^1$ is hydrogen or includes a targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl; $R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof; and a pharmaceutically acceptable carrier.

In other embodiments, $R^1$-$R^{16}$ are independently selected from hydrogen, halogen, nitro, cyano, hydroxyl, thiol, amino, and methyl.

In some embodiments, the phthalocyanine compound or targeted conjugate thereof can have the formula (II):

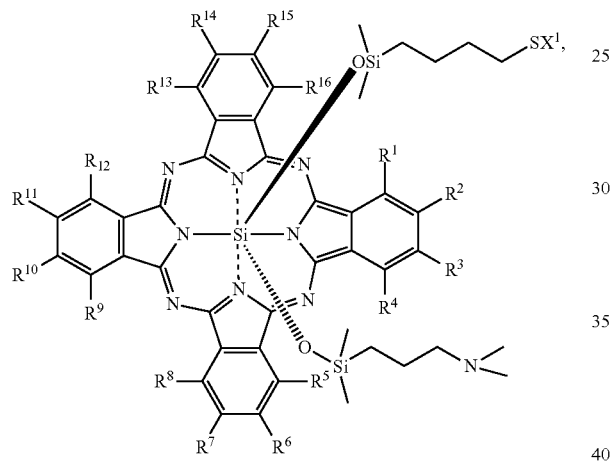

wherein $X^1$ is hydrogen or includes a targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In still other embodiments, the phthalocyanine compound or targeted conjugate thereof can have the formula (III):

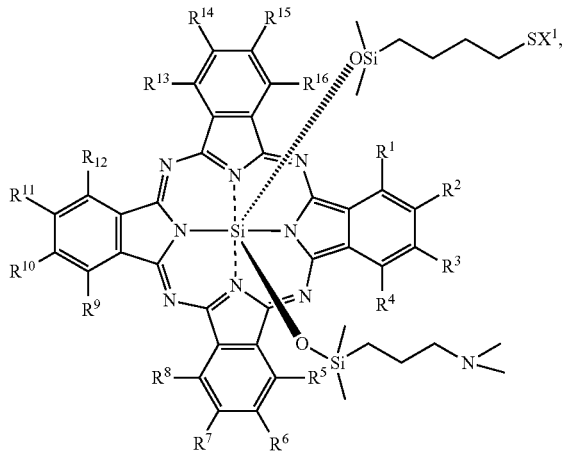

wherein $X^1$ is hydrogen or includes a targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In certain embodiments, the phthalocyanine compound or targeted conjugate thereof has the formula (IV):

(IV)

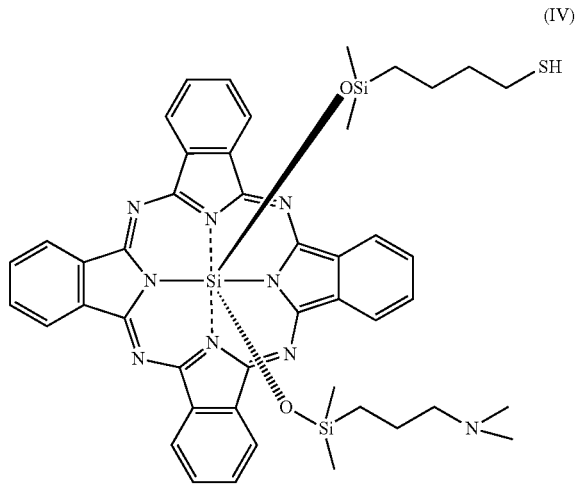

or pharmaceutically acceptable salt thereof.

The phthalocyanine compound can be coupled or conjugated to the targeting moiety. The targeting moiety can be selected from the group consisting of a polypeptide, polynucleotide, small molecule, elemental compound, antibody, and antibody fragments. In some embodiments, the targeting moiety is linked to the thiol group of the phthalocyanine compound.

In some embodiments, the targeting moiety can include a pyridine-2-ylmethylamino acetic acid (PAMA) ligand, such as a PSMA-1 ligand.

BRIEF DESCRIPTION OF THE DRAWINGS

The following is a brief description of the drawings which are presented for the purpose of illustrating the invention and not for the purpose of limiting them.

FIGS. 5(A-B) illustrate in vitro cellular uptake results of PSMA-1-Pc413 (A) and PSMA-1-IR700 (B). PSMA positive PC3pip cells and PSMA negative PC3flu cells on coverslips were incubated with no probe (0 minute) or 1 μM of PSMA-1-PDT for 15 minutes, 30 minutes, 1 hour and 4 hours. Nuclei were stained using DAPI (false color blue) and uptake of PSMA-1-PDT was assessed by fluorescence microscopy (false color red). Specificity of PSMA-1-PDT for PSMA binding was evaluated by incubation of PC3pip and PC3flu cells with 1 μM of PSMA-1-PDT and 10 μM of Cys-CO-Glu, last column. Signal in PC3pip cells was significantly competed by Cys-CO-Glu, suggesting the binding of PSMA-1-Pc413 to PSMA is specific. Images are taken at 40×. Representative images are shown from three independent experiments.

FIGS. 6(A-D) illustrate: (A) Phototoxicity of PSMA-1-Pc413. PC3pip and PC3flu cells were incubated with different concentrations of PSMA-1-Pc413 or Pc413 at 37° C. for 1 hour in RPMI medium, cells were then treated by light with radiant exposure at 0.5 J/cm². PSMA-1-Pc413 showed selective PDT activity in PSMA-positive PC3pip cells (*: P<0.05). Values are mean±SD of 8 replicates. (B) Phototoxicity of PSMA-1-IR700. PC3pip and PC3flu cells were incubated with 1 μM of PSMA-1-IR700 or IR700 at 37° C. for 4 hours in RPMI medium, the cells were then kept in dark or exposed to light with different radiant exposure. However, no phototoxicity was observed. Values are mean±SD of 8 replicates. (C) Generation of singlet oxygen by PSMA-1-Pc413 and PSMA-1-IR700 in PBS. Generation of singlet oxygen was detected by the indirect DPBF method. The absorbance at 411 nm decreased significantly when PSMA-1-Pc413 or PSMA-1-IR700 in PBS was added to DPBF solution and light irradiation was applied, suggesting a high efficacy in generation of reactive $^1O_2$. Values are mean±SD of 3 replicates. (D) Generation of singlet oxygen by PSMA-1-Pc413 and PSMA-1-IR700 in RPMI1640 media. PSMA-1-Pc413 can effectively generate singlet oxygen in RPMI media as shown by the reduced absorbance at 411 nm, however, PSMA-1-IR700 was not as good in generating single oxygen in RMPI1640 media as in PBS. Values are mean±SD of 3 replicates.

FIGS. 7(A-D) illustrate imaging of PSMA-1-Pc413 in mice bearing flank PC3pip and PC3flu tumors. (A) In vivo Maestro imaging of a typical mouse treated with PSMA-1-Pc413. Mice received 1 nmol of PSMA-1-Pc413 via tail vein injection and then were imaged at the designated times. Representative images are shown of N=5. (B) Ex vivo imaging of mice organs at 5 days post-injection of PSMA-1-Pc413. The fluorescent signal in PC3pip tumor was significantly higher than in other organs. (C) In vivo Maestro imaging of mice injected with 1 nmol of PSMA-1-Pc413 and 1000 nmol of a selective PSMA receptor binding molecule, ZJ-MCC-Ahx-YYYG. Blockade of fluorescent uptake in PC3pip tumors was observed. (D) Quantification of fluorescent signal intensity in PC3pip and PC3flu tumors from the mice used in FIGS. 7A and 7C. Values represent mean±SD of 5 animals.

FIGS. 8(A-D) illustrate imaging of PSMA-1-IR700 in mice bearing flank PC3pip and PC3flu tumors. (A) In vivo Maestro imaging of mice treated with PSMA-1-IR700. Mice received 1 nmol of PSMA-1-IR700 through tail vein injection and then were imaged at the indicated time points. Representative images of N=5 mice are shown. Selective uptake in PC3pip tumors was observed. (B) Ex vivo imaging of mice organs at 48-hour post-injection of PSMA-1-IR700. The fluorescent signal in PC3pip tumor was significantly higher than in other organs. (C) In vivo Maestro imaging of mice injected with 1 nmol of PSMA-1-IR700 and 1000 nmol of PSMA-1. Blockade of fluorescent uptake in PC3pip tumors was observed. (D) Fluorescent signal quantification of PSMA-1-IR700 in PC3pip and PC3flu tumors from mice used in FIGS. 8A and 8C. Values represent mean±SD of 5 animals.

FIGS. 9(A-F) illustrate the In vivo photodynamic treatment of PSMA-positive PC3pip tumors. Values represent mean±SD of 5 animals. (A) Quantification of PSMA-1-Pc413 fluorescent signal in PC3pip tumors. Signal in PC3pip tumors increased when mice received increased dose of PSMA-1-Pc413. (B) Loss of fluorescent signal in PC3pip tumors after PSMA-1-Pc413 PDT treatment. Mice received 0.5 mg/kg PSMA-1-Pc413 and were treated by laser light (672 nm) with radiant exposure of 150 J/cm² at 24-hour post-injection. Tumor is indicated by the red circle. This loss of fluorescence after PDT indicated the activation of PSMA-1-Pc413 by light. (C) Tumor growth inhibition by PSMA-1-Pc413 PDT treatment in PC3pip tumors. Tumors were irradiated with 150 J/cm² light (672 nm) at 24-hour post-injection (red arrow). Significant tumor regression was observed and the response was dose-dependent. Values represent mean±SD of 5 tumors. P values are obtained by comparison with control group (*: P<0.05). (D) Quantification of PSMA-1-IR700 fluorescent signal in PC3pip tumors. Signal in PC3pip tumors increased when mice received increased dose of PSMA-1-IR700. (E) Loss of fluorescent signal in PC3pip tumors after PSMA-1-IR700 PDT treatment. Mice received 0.5 mg/kg PSMA-1-IR700 and were treated by light (690 nm) with radiant exposure at 50 J/cm² at 1-hour post-injection. Tumor is indicated by the red circle. This loss of fluorescence after PDT indicated the activation of PSMA-1-IR700 by light. (F) Tumor growth inhibition by PSMA-1-IR700 PDT treatment in PC3pip tumors. Mice received PSMA-1-IR700 on days 0, 4 and 8 (red arrows). PDT treatment was performed at 1-hour post-injection. Significant tumor regression was observed and the response was dose-dependent. Values represent mean±SD of 5 tumors. P values are obtained by comparison with control group (*: P<0.05).

FIGS. 10(A-D) illustrate a histological analysis of PC3pip tumors. Cell damage was observed in PDT treated PC3pip tumors as compared to non-treatment controls. (A) Control PC3pip tumor receiving PSMA-1-PC413. Mice received 0.5 mg/kg of PSMA-1-PC413 and tumors were taken out at 48-hour post-injection without light irradiation. (B) PC3pip tumors receiving PSMA-1-Pc413 and treated with light.

Figure 1:
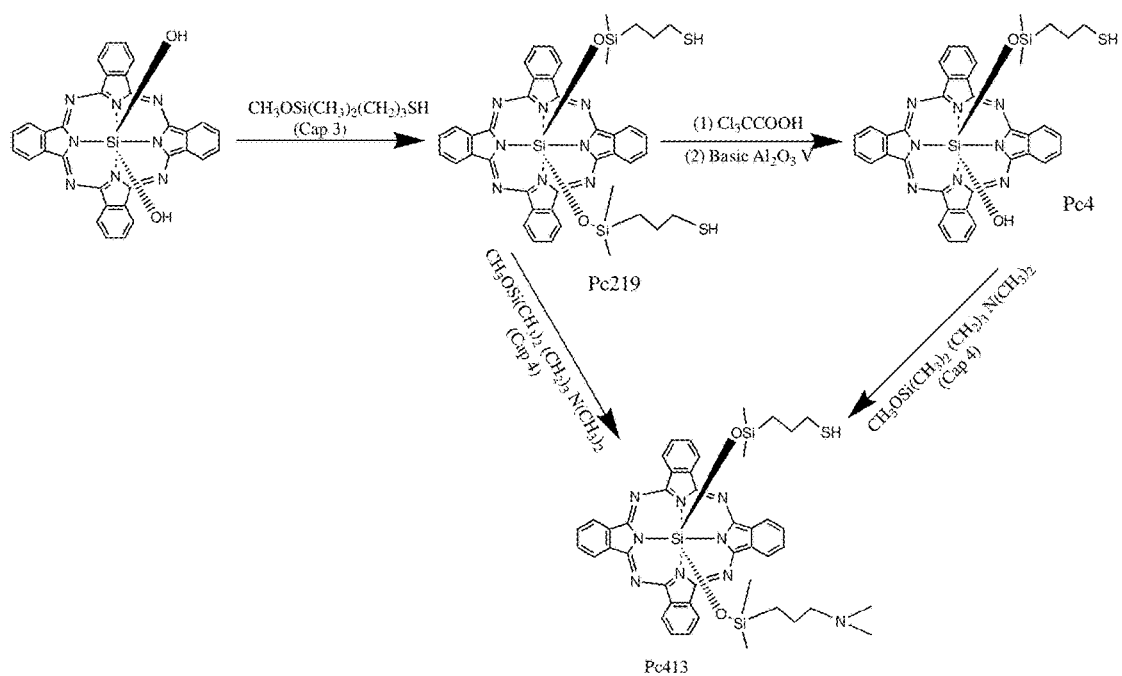
FIG. 1 illustrates a synthesis scheme for Pc413.

Mice received 0.5 mg/kg of PSMA-1-PC413, irradiated with light with radiant exposure at 150 J/cm$^2$ light at 24-hour post-injection. Tumors were taken out at 24 hour post PDT treatment. (C) Control PC3pip tumor receiving PSMA-1-IR700. Mice received 0.5 mg/kg of PSMA-1-IR700 and tumors were taken out at 24-hour post-injection without light irradiation. (D) PC3pip tumors receiving PSMA-1-IR700 and treated with light. Mice received 0.5 mg/kg of PSMA-1-IR700, and treated by light with radiant exposure at 50 J/cm$^2$ light at 1-hour post-injection. Tumors were taken out at 24-hour post PDT treatment.

DETAILED DESCRIPTION

All scientific and technical terms used in this application have meanings commonly used in the art unless otherwise specified. The definitions provided herein are to facilitate understanding of certain terms used frequently herein and are not meant to limit the scope of the application.

The term "alkoxy" refers to an alkyl group having an oxygen attached thereto. Representative alkoxy groups include methoxy, ethoxy, propoxy, tert-butoxy and the like. An "ether" is two hydrocarbon groups covalently linked by an oxygen. Accordingly, the substituent of an alkyl that renders that alkyl an ether is or resembles an alkoxy.

The terms "amine" and "amino" are art-recognized and refer to both unsubstituted and substituted amines and salts thereof.

The term "aryl" as used herein includes 5-, 6-, and 7-membered substituted or unsubstituted single-ring aromatic groups in which each atom of the ring is carbon. Aryl groups include benzene, phenol, aniline, and the like.

The terms "carbocycle" and "carbocyclyl", as used herein, refer to a non-aromatic substituted or unsubstituted ring in which each atom of the ring is carbon.

The terms "heteroaryl" includes substituted or unsubstituted aromatic 5- to 7-membered ring structures, more preferably 5- to 6-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms.

The term "substituted" refers to moieties having substituents replacing a hydrogen on one or more carbons of the framework. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Substituents on fused ring structures can be peripheral or non-peripheral substituents. A non-peripheral substituent, as defined herein, is a substituent which is adjacent (i.e., α) to the point of fusion between an outer phenyl ring and an inner pyrrole ring, as found in phthalocyanine compounds as exemplified by Formula (I) herein. A substituent is peripheral, on the other hand, when it is not a non-peripheral substitutent. For example, in Formula I provided herein, the substituents $R^2$, $R^3$, $R^6$, $R^7$, $R^{10}$, $R^{11}$, $R^{14}$, and $R^{15}$ are peripheral substituents.

As used herein, the term "targeting moiety" can refer to a molecule or molecules that are able to bind to and complex with a biomarker. The term can also refer to a functional group that serves to target or direct a compound described herein to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As used herein, the term "tumor" can refer to an abnormal mass or population of cells that result from excessive cell division, whether malignant or benign, and all pre-cancerous and cancerous cells and tissues.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition. As used herein, the terms "treating" or "treatment" of a neoplastic disorder can refer to executing a treatment protocol to eradicate at least one neoplastic cell. Thus, "treating" or "treatment" does not require complete eradication of neoplastic cells.

"PSMA" refers to Prostate Specific Membrane Antigen, a potential carcinoma marker that has been hypothesized to serve as a target for imaging and cytotoxic treatment modalities for cancer.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment.

Embodiments described herein relate to phthalocyanine compounds or targeted conjugates thereof for use in diagnostic, therapeutic, and theranostic applications and particularly for use in photodynamic therapy (PDT). The phthalocyanine compounds disclosed herein, are analogs of the PDT photosensitizing drug Pc4, and have been found to be effective in targeted bioimaging and targeted PDT of cancer in a subject.

In some embodiments, the phthalocyanine compounds or targeted conjugates thereof can have the following formula (I):

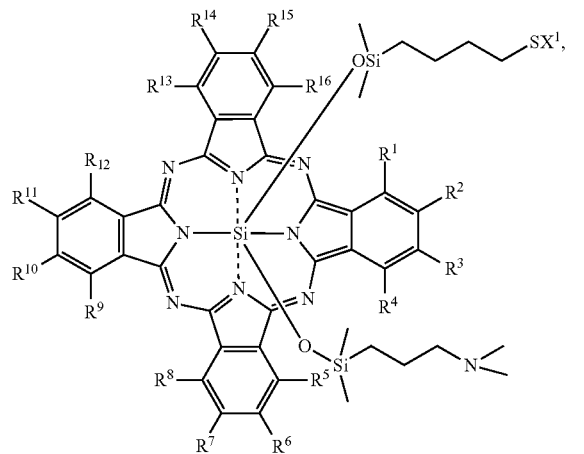

wherein $X^1$ is hydrogen or includes a targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;
$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In certain embodiments, $R^1$-$R^{16}$ of the compound of formula (I) are independently selected from the group consisting of hydrogen, halogen, nitro, cyano, hydroxyl, thiol, amino, and methyl, while in other embodiments $R^1$-$R^{16}$ are all hydrogen.

In other embodiments, the phthalocyanine compound or targeted conjugate thereof can have the formula (II):

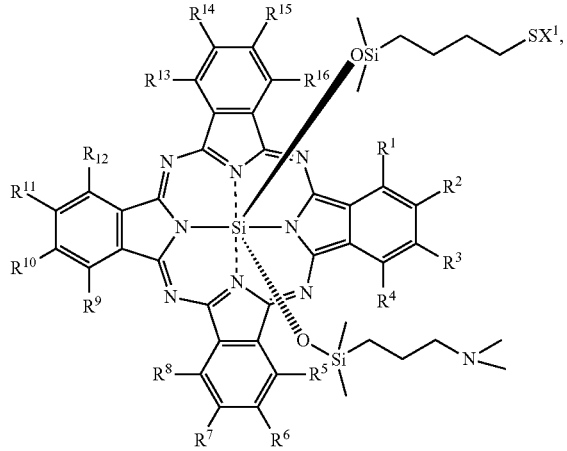

wherein $X^1$ is hydrogen or includes a targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;
$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In still other embodiments, the phthalocyanine compound or targeted conjugate thereof can have the formula (III):

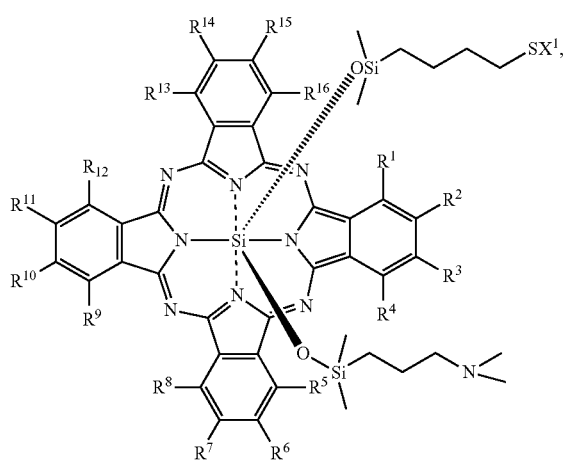

wherein $X^1$ is hydrogen or includes a targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In certain embodiments, the phthalocyanine compound of formula (I) can have the formula:

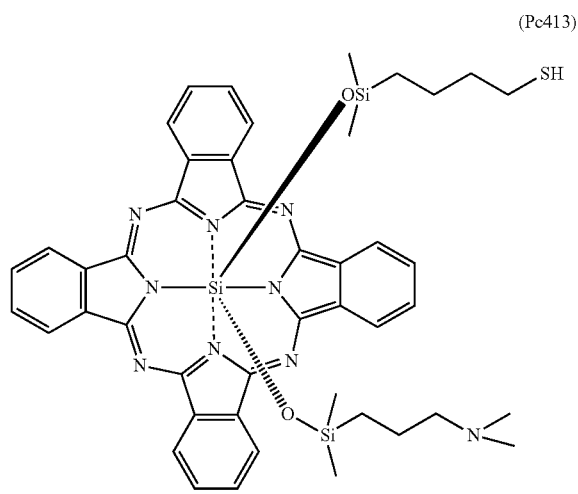

(Pc413)

or pharmaceutically acceptable salts thereof.

A synthetic scheme for producing the phthalocyanine compound in accordance with one embodiment of the invention is illustrated in FIG. 1.

In some embodiments, the phthalocyanine compound can additionally or optionally be indirectly or directly coupled or conjugated to at least one targeting moiety to target and/or adhere the phthalocyanine compound to a cell or tissue of interest. The targeted conjugate including the phthalocyanine compound and the targeting moiety can be administered to a subject for diagnostic, therapeutic, and/or theranostic applications.

The targeting moiety can include any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer, such as prostate specific membrane antigen (PSMA), CA-125 receptor, epidermal growth factor receptor, and transferrin receptor. The targeting moiety can interact with the biomarkers through non-covalent binding, covalent binding, hydrogen binding, van der Waals forces, ionic bonds, hydrophobic interactions, electrostatic interaction, and/or combinations thereof.

The targeting moiety can be directly or indirectly coupled or conjugated to the axial thiol group or terminating ligand attached to the central silicon metalloid of the phthalocyanine compound of formula (I). In some embodiments, the phthalocyanine compound can be indirectly coupled or conjugated to the targeting moiety via a linker. The linker can be of any suitable length and contain any suitable number of atoms and/or subunits. The linker can include one or a combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

The targeting moiety can include, but is not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating antibodies. These methods typically include the step of immunization of animals, typically mice, with a desired immunogen (e.g., a desired target molecule or fragment thereof). Once the mice have been immunized and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

The targeting moiety need not originate from a biological source. The targeting moiety may, for example, be screened from a combinatorial library of synthetic peptides. One such method is described in U.S. Pat. No. 5,948,635, incorporated herein by reference, which describes the production of phagemid libraries having random amino acid insertions in the pIII gene of M13. These phage may be clonally amplified by affinity selection.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moiety may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, the antibodies or variants thereof may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature, 321, 522-525 or Tempest et al. (1991), Biotechnology, 9, 266-273. Also, transgenic mice, or other mammals, may be used to express humanized antibodies. Such humanization may be partial or complete.

In certain embodiments, a targeting moiety as described herein may comprise a homing peptide, which selectively directs the pthalocyanine compound to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274: 11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264, 563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In still other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated that mimic those residues, which facilitate the interaction. Such mimetics may then be used as a targeting moiety to deliver the phthalocyanine compound to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

In other embodiments, the targeting moiety may comprise a ligand molecule, including, for example, ligands which naturally recognize a specific desired receptor of a target cell. Such ligand molecules include ligands that have been modified to increase their specificity of interaction with a target receptor, ligands that have been modified to interact with a desired receptor not naturally recognized by the ligand, and fragments of such ligands.

By way of example, where the cell targeted is a prostate cancer cell, the targeting moiety can comprise a PSMA ligand. PSMA is highly expressed in prostate cancer expression. PSMA-targeted PDT agents can provide image guidance for prostate tumor resection and allow for subsequent PDT to eliminate unresectable or remaining cancer cells. In certain embodiments, the targeting moiety can comprise a highly negatively charged PSMA ligand (e.g., PSMA-1) for PSMA-targeted imaging of prostate cancer PSMA-1 ligand.

The phthalocyanine compound or targeted conjugate thereof can be provided in a pharmaceutical composition with pharmaceutically acceptable carrier. "Pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In some embodiments, aqueous-based or oil-based pharmaceutically acceptable carriers can be used. An aqueous-based pharmaceutically acceptable carrier is a polar solution primarily consisting of water, and including solutions such as pyrogen-free water, isotonic saline, Ringer's solution, and phosphate buffer solutions. Oil-based pharmaceutically acceptable carriers, on the other hand, are relatively non-polar solutions consisting primarily of oils or other relatively non-polar organic solvents. Examples of oil-based pharmaceutically acceptable carriers include various organic solvents, mineral oil, vegetable oil, and petrolatum.

In some embodiments, pharmaceutical compositions including the phthalocyanine compounds or targeted conjugate thereof can be formulated for systemic or topical administration. Systemic administration includes delivery of an aqueous solution, preferably a buffered aqueous solution, including a phthalocyanine compound or targeted conjugate thereof. Systemic formulations typically also include a dispersant. Systemic administration is typically done parenterally (e.g., intravenously or intramuscularly). However, systemic administration can also be carried out by oral administration. By way of example, a phthalocyanine composition can be intravenously administered to a subject that is known to or suspected of having a tumor.

Topical administration of phthalocyanine compounds or targeted conjugate thereof can be accomplished using various different formulations such as powders, sprays, ointments, pastes, creams, lotions, gels, solutions, or patches. The active component may be mixed under sterile conditions with a pharmaceutically acceptable carrier, and with any preservatives, buffers, or propellants which may be required. The ointments, pastes, creams, solutions, foams, lacquers, oils and gels may contain excipients in addition to phthalocyanine(s). These formulations may contain a phthalocyanine salt within or on micro or nanoparticles, liposomes, beads, polymer matrices, sponges, osmotic pumps, or other structures.

Phthalocyanine compounds or targeted conjugate thereof can be formulated as ointments or creams for topical administration. Ointments are homogeneous, semi-solid preparations intended for external application to the skin or mucous membranes. They are used as emollients or for the application of active ingredients to the skin for protective, therapeutic, or prophylactic purposes and where a degree of occlusion is desired. Ointments can be formulated using hydrophobic, hydrophilic, or water-emulsifying bases to provide preparations for various applications. Creams, on the other hand, are semi-solid emulsions; i.e., a mixture of oil and water. They are divided into two types: oil-in-water creams which are composed of small droplets of oil dispersed in a continuous aqueous phase, and water-in-oil creams which are composed of small droplets of water dispersed in a continuous oily phase.

Phthalocyanines compounds or targeted conjugate thereof can also be administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers.

Phthalocyanine compounds or targeted conjugate thereof can also be formulated for delivery as a gel. Gel formulations comprising a phthalocyanine compound or salt thereof may be prepared according to U.S. Pat. No. 6,617,356 or U.S. Pat. No. 5,914,334, the disclosures of which are incorporated herein in their entirety. In addition, phthalocyanine-containing gels can be dried to form films suitable for phthalocyanine administration.

Transdermal patches have the added advantage of providing controlled delivery of a phthalocyanine to the body. Such dosage forms can be made by dissolving or dispersing the agent in the proper medium. Absorption enhancers can also be used to increase the flux of the photosensitizer(s) into the skin. The rate of such flux can be controlled by either providing a rate controlling membrane or dispersing the agent in a polymer matrix or gel.

Phthalocyanine compounds or targeted conjugate thereof can also be delivered transdermally using microneedles. See for example Arora et al., International Journal of Pharmaceutics, 364, pg. 227-236 (2008), which describes microscale devices for transdermal drug delivery.

Delivery of phthalocyanines compounds or targeted conjugate thereof described herein across an epithelial, epidermal, serosal or mucosal surface may be accomplished using application of an electrical current and a charged solvent solution, such as iontophoresis.

In some embodiments, the phthalocyanine compounds or targeted conjugate thereof described herein can be used in photodynamic therapy (PDT) to treat a subject. Methods for conducting photodynamic therapy are known in the art. See for example Thierry Patrice. *Photodynamic Therapy;* Royal Society of Chemistry, 2004. Pharmaceutical composition including a phthalocyanine compound or targeted conjugate thereof can be applied to an organ or tissue as a step in PDT. In certain embodiments, the composition can be applied to an epithelial, mesothelial, synovial, fascial, or serosal surface, including, but not limited to, the eye, esophagus, mucous membrane, bladder, joint, tendon, ligament, bursa, gastrointestinal, genitourinary, pleural, pericardial, pulmonary, or uroepithelial surfaces.

In other embodiments, a pharmaceutical composition including a phthalocyanine compound or targeted conjugate thereof can be used in a method for treating cancer. In the method, the pharmaceutical composition can be applied or administered to a surface of cancerous tissue and the surface can then be irradiated to treat the cancer. In some embodiments, the surface can be skin in the case of skin cancer, or an exposed internal surface in the case of other types of cancer.

Pharmaceutical compositions including phthalocyanines compounds or targeted conjugate thereof can also be used to treat various other diseases or disorders. For example, pharmaceutical compositions including phthalocyanine compounds can be used to purge bone marrow for autologous bone marrow transplantation, purge viruses from whole blood or blood components, treat psoriasis, treat warts, treat macular degeneration, or treat intra-arterial plaques.

Phthalocyanines compound or targeted conjugate thereof can be formulated to allow delivery in sufficient amounts and for a period of time(s) to be therapeutically effective. In some embodiments, the therapeutically effective amount is the amount required to label cancer cells in the subject. Single or multiple administrations of the probe can be given.

A pharmaceutical composition including a phthalocyanine compound or targeted conjugate thereof described herein can be administered to a subject in a detectable and/or imaging effective quantity. A "detectable quantity" means that the amount of the detectable compound that is administered is sufficient to enable detection of binding of the phthalocyanine compound to the targeted cell or tissue, e.g., a cancer cell. An "imaging effective quantity" means that the amount of the detectable compound that is administered is sufficient to enable imaging of binding of the compound to the targeted cells.

In some embodiments, the pharmaceutical composition including a phthalocyanine compound or targeted conjugate thereof described herein can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue. The ROI can include regions to be imaged for both diagnostic and therapeutic purposes. The ROI is typically internal; however, it will be appreciated that the ROI may additionally or alternatively be external.

At least one image of the ROI can be generated using an imaging modality. The imaging modality can include one or combination of known imaging techniques capable of visualizing the phthalocyanine compound or targeted conjugate thereof. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET). The imaging modality can then be operated to generate a visible image of the ROI. In a subject known to or suspected of having a tumor, for example, an ultrasonic transducer can be applied to at least a portion of the ROI to image the target tissue. A visible image of the tumor can then be obtained, such that the presence, absence, and/or extent of a particular neoplastic disorder can be ascertained. It will be appreciated that the imaging modality may be used to generate a baseline image prior to administration of the composition. In this case, the baseline and post-administration images can be compared to ascertain the presence, absence, and/or extent of a particular disease or condition.

In some embodiments, pharmaceutical compositions including the phthalocyanine compounds or targeted conjugate thereof can be administered to a subject to treat and/or image a neoplastic disease in subject. Neoplastic diseases can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells.

In certain embodiments, a pharmaceutical composition including a phthalocyanine compound or targeted conjugate thereof and a pharmaceutically acceptable carrier described herein administered to a subject can be used to determine the presence, location, and/or distribution of cancer cells, i.e., PSMA expressing cancer cells or PSMA expressing neovaculature of the cancer cells, in an organ or body area of a patient. The presence, location, and/or distribution of the targeting moiety coupled to a detectable phthalocyanine compound in the animal's tissue, e.g., prostate tissue, can be visualized (e.g., with an in vivo imaging modality). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the targeting moiety coupled to a detectable phthalocyanine compound may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one embodiment, compositions including a phthalocyanine compound and a targeting moiety described herein may be administered to a subject to assess the distribution of targeted cancerous tumor cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of targeted tissue on the tumor margin that are outside the tumor edge that appear to be grossly normal but are infiltrated by dispersing tumor cells upon histological examination.

The compositions described herein can be used in intra-operative imaging techniques to guide surgical resection and eliminate the "educated guess" of the location of the tumor by the surgeon. Previous studies have determined that more extensive surgical resection improves patient survival. Thus, the compositions described herein that function as diagnostic molecular imaging agents have the potential to increase patient survival rates.

The specific process utilized to synthesize the phthalocyanine compounds and phthalocyanines with attached targeted moieties of the present invention, and the enhanced results produced through the use of these new compounds for photodynamic therapy, are more particularly described below in the following examples. The following example is for the purpose of illustration only and is not intended to limit the scope of the claims, which are appended hereto.

EXAMPLE 1

In this Example, we show PSMA-targeted PDT agents can be used for surgical guidance and to allow for subsequent PDT to eliminate un-resectable or "missed" cancer cells. Previously, we have developed a peptide-based, highly negatively charged PSMA ligand (PSMA-1) for PSMA-targeted imaging of prostate cancer. In this study, we have designed two PSMA-1 based PDT conjugates (PSMA-1-PDT), PSMA-1-Pc413 (FIG. 3) and PSMA-1-IR700 (FIG. 4). Pc413 (FIG. 1) is an analogue of the second generation phthalocyanine PDT drug Pc4 which is currently in clinical trials, and IR700 (FIG. 4) is a commercially available near-infrared phthalocyanine dye which has PDT activity. The two conjugates reported here were found to be effective as theranostic conjugates, allowing both targeted-bioimaging and targeted-PDT of prostate cancer.

Synthesis of Pc 413 (FIG. 1)

Preparation of CH3OSi(CH3)2(CH2)3SH (cap3)

Under Ar, a 0° C. solution of 3-mercaptopropyltrimethoxysilane (8.5 g) and tetrahydrofuran (50 mL) was treated dropwise with a $CH_3MgCl$-tetrahydrofuran solution (50 mL). The reaction mixture was stirred for 1 h and then treated dropwise with $CH_3OH$ (40 mL), both being done at low temperature (0° C.), diluted with a tetrahydrofuran-diethyl ether solution (1:8, 90 mL), and filtered. The solid was washed (diethyl ether), and the washings and filtrate were combined and concentrated by rotary evaporation at room temperature. The concentrate was distilled (60 torr, 90-110° C.) and weighed (3.8 g, 54%). $^1H$ NMR ($C_6D_6$): d 3.21 (s, $^3H$, $OCH_3$), 2.24 (q, $^2H,Si(CH_2)_2CH_2$), 1.49 (m, $^2H$, $SiCH_2CH_2$), 1.14 (t, $^1H$, SH), 0.47 (m, $^2H,SiCH_2$), 0.04 (s, $^6H$, $SiCH^3$) Cap 3 is a colorless liquid.

Preparation of SiPc[OSi(CH3)2(CH2)3SH]2 (Pc93)

Under Ar, a mixture of SiPc(OH)2 (135 mg, Sigma-Aldrich), cap 3 (1.60 g), and pyridine (80 mL) was distilled (5 mL of distillate) for 1 h, and evaporated to dryness by rotary evaporation (30° C.). The solid was chromatographed (basic-$Al_2O_3$ III, $CH_2Cl_2$-ethyl acetate solution, 5:1), air-dried, and weighed (190 mg, 96%). UV-Vis (toluene) kmax, nm: 669. $^1H$ NMR ($C_6D_6$): d 9.72 (m, $^8H$, 1, 4-Pc H), 7.87 (m, $^8H$, 2, 3-Pc H), 0.91 (q, $^4H,Si(CH_2)_2CH_2$), 0.39 (t, $^2H$, SH),) 1.02 (m, $^4H$, $SiCH_2CH_2$,) 2.22 (t, $^4H$, $SiCH_2$,) 2.68 (s, $^{12}H$, $SiCH_3$). $^{13}C$ NMR ($CDCl_3$): d 148.9 (5-Pc C), 136.3 (4a-Pc C), 131.1 (2, 3-Pc C), 123.9 (1, 4-Pc C), 27.1(Si $(CH_2)_2CH_2$), 27.0 ($SiCH_2CH_2$), 15.3 ($SiCH_2$), 3.2 ($SiCH_3$). Pc 93 is a blue solid. It is soluble in $CH_2Cl_2$, dimethylformamide and toluene, and insoluble in hexanes.

Preparation of HOSiPcOSi(CH3)2(CH2)3SH (Pc219)

A mixture of phthalocyanine Pc 93 (114 mg) and a solution of trichloroacetic acid (150 mg) in $CH_2Cl_2$ (100 mL) was stirred at room temperature for 1.5 h, treated with pyridine (20 mL) and then $H_2O$ (100 mL), and separated. The aqueous portion of the reaction product was washed ($CH_2Cl=$), and the washings and the organic portion of the reaction product were combined and concentrated by rotary evaporation (room temperature). The concentrate was passed down an $Al_2O_3$ column (basic-Al2O3 V, CH2Cl2-ethyl acetate solution, 10:1), and evaporated to dryness by rotary evaporation (room temperature). The solid was washed (acetonitrile), air-dried and weighed (52 mg, 50%). UV-Vis (toluene) kmax, nm: 680. $^1H$ NMR ($C_6D_6$): d 9.67 (m, $^8H$, 1, 4-Pc H), 7.84 (m, $^8H$, 2, 3-Pc H), 0.90 (q, $^2H$, $Si(CH_2)_2CH_2$), 0.36 (t, $^1H$, SH),) 1.00 (m, $^2H$, $SiCH_2CH_2$,) 2.19 (t, $^2H$, $SiCH_2$,) 2.64 (s, $^6H$, $SiCH_3$). $^{13}C$ NMR ($CDCl_3$): 149.9 (5-Pc C), 135.8 (4a-Pc, C), 131.6 (2, 3-Pc, C), 124.2 (1, 4-Pc, C), 27.0 ($Si(CH_2)_2CH_2$), 26.8 ($SiCH_2CH_2$), 15.0 ($SiCH_2$,) 3.2 ($SiCH_3$). HRMS-MALDI (m/z): [M-OH]+ calcd for $C_{37}H_{29}N_8OSSi_2$, 689.1724; found 689.1690. Pc 219 is a blue solid. It is soluble in $CH_2Cl_2$, dimethylformamide and toluene, and insoluble in hexanes.

Preparation of CH3OSi(CH3)2(CH2)3N(CH3)2 (cap 4)

Under argon gas a solution of $CH_3MgCl$ in tetrahydrofuran (3.0 M, 45 mL) was added dropwise to a cool (ice bath) solution of $(CH_3O)_3Si(CH_2)_3N(CH_3)_2$ (11 mL) in tetrahydrofuran (100 mL), and the resulting suspension was stirred for 2 hours while being kept cool at about 5° C.). Methanol (20 mL) then was added to the suspension and the mixture formed was filtered. The solid was washed with ether (50 mL) and the washings and filtrate were combined and concentrated with a rotary evaporator (45° C.). The concentrate was fractionally distilled under vacuum (45 torr) and a selected fraction (86-88° C., 5.0 g.) was retained (55%): NMR (CDCl$_3$) δ 3.42 (s, CH$_3$O), 2.24 (m, γ-CH$_2$), 2.20 (s, NCH$_3$), 1.49 (m, β-CH$_2$), 0.57 (m, α-CH$_2$), 0.10 (s, CH$_3$Si). The compound is a colorless liquid.

Preparation of HS(CH$_2$)$_3$Si(CH$_3$)$_2$OSiPcOSi(CH$_3$)$_2$(CH$_2$)$_3$N(CH$_3$)$_2$ (Pc 413)

A mixture of Pc 219 (96 mg, 0.14 mmol), cap 4 (37 mg, 0.21 mmol), and pyridine (40 mL) was slowly refluxed for 1 hr (distillate 15 mL) under N$_2$, and concentrated by rotary evaporation (8 torr, room temperature). The solid was chromatographed (basic Al$_2$O$_3$ (III), CH$_2$Cl$_2$:ethyl acetate, 5:1), evaporated to dryness by rotary evaporation (room temperature), vacuum dried (room temperature), and weighed (42 mg, 0.049 mmol, 35%).

Alternatively, a mixture of Pc 93 (144 mg, 0.17 mmol), cap 4 (218 mg, 0.21 mmol), and pyridine (50 mL) was slowly refluxed for 1 hr (distillate 20 mL) under N$_2$, and concentrated by rotary evaporation (8 torr, room temperature). The solid was chromatographed (basic Al$_2$O$_3$ (III), CH$_2$Cl$_2$:ethyl acetate, 5:1), evaporated to dryness by rotary evaporation (room temperature), vacuum dried (room temperature), and weighed (58 mg, 0.068 mmol, 40%).

Synthesis of PSMA-1-Pc413
Synthesis of PSMA-1 Ligand

PSMA-1 was synthesized manually using standard Fmoc chemistry. Generally, peptide was synthesized at 0.2 mmol scale starting from C-terminal Fmoc-rink amide MBHA resin. Fmoc-deprotection at each cycle was carried out using 20% piperidine in DMF. Coupling reactions were carried out using 3.3 equiv of Fmoc-amino acids in DMF activated with 3.3 equiv of HCTU and 5 equiv of diisopropylethylamine (DIPEA) in DMF. These steps were repeated each time with an amino acid added. After the peptide sequence Fmoc-Glu'-Amc-Ahx-Glu-Glu-Glu-Lys(Mtt) was built on the resin, the Fmoc group of N-terminal amino acid Glu' was deprotected by 20% piperidine. Then, a chloroform solution containing 3 eq. of H-Glu(OtBu)-OtBu mixed with 2.5 eq. of DIPEA were prepared. The solution is then added slowly to 0.25 eq. triphosgene in chloroform over 10 minutes at room temperature. After 15 minute incubation, the reaction mixture was mixed with Glu'-Amc-Ahx-Glu-Glu-Glu-Lys on rink amide resin pre-swollen in chloroform with 2.5 eq. of DIPEA. After the reaction was complete, the resin was washed with DMF and then dichloromethane and dried. The peptide was cleaved from resin by TFA/water/triisopropylsilane (950:25:25). The cleaved peptide was purified by preparative HPLC. The products were ascertained by high resolution matrix-assisted laser desorption/ionization mass (MALDI-MS) spectra from an Applied Biosystem 4800 MALDI TOF/TOF Analyzer using positive ion mode. Retention time: 18.6 min. MALDI MS: C$_{48}$H$_{74}$N$_{10}$O$_{20}$, 1087.5 (found); 1087.1 (calculated).

Figure 2:
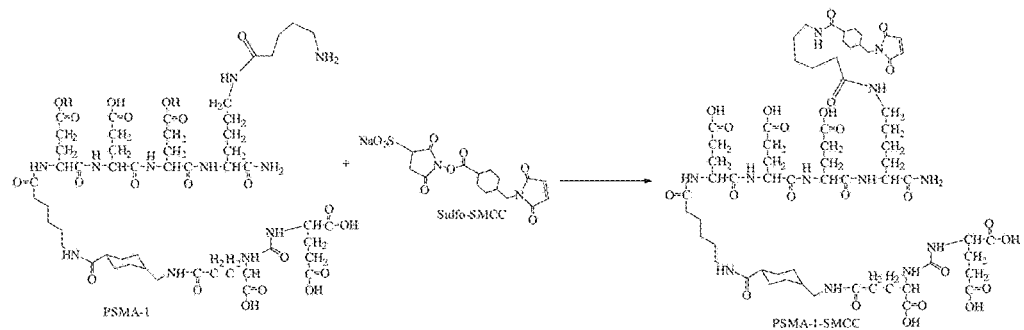
FIG. 2 illustrates a synthesis scheme for PSMA-1-SMCC.

Synthesis of PSMA-1-SMCC (FIG. 2)

Coupling of PSMA-1 to sulfosuccinimidyl-4-(N-maleimidomethyl)cyclohexane-1-carboxylate (sulfo-SMCC) (Thermo Scientific) was performed in 100 mM phosphate buffer, pH 7.0. PSMA-1 (200 nmol) was dissolved in 100 μL of phosphate buffer; then 400 nmol of sulfo-SMCC in 500 μL of phosphate buffer was added. The reaction mixture was left at room temperature overnight. The crude product was purified by preparative HPLC. Yield: 78%. Retention time: 24.8 min. MALDI-MS: C$_{58}$H$_{87}$N$_{11}$O$_{23}$, 1306.7 (found); 1306.4 (calculated). PSMA-1-SMCC can also be synthesized on the resin by removing the MTT group from the lysine, then have the free NH2 couple to SMCC.

Figure 3:
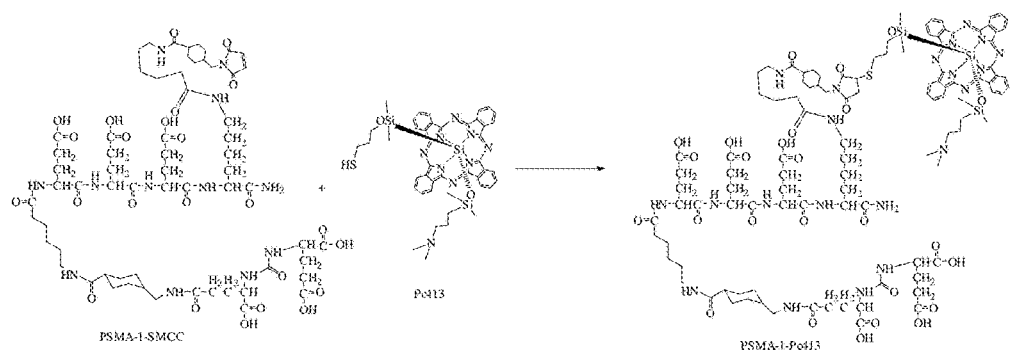
FIG. 3 illustrates a synthesis scheme for PSMA-1-Pc413.
Figure 4:
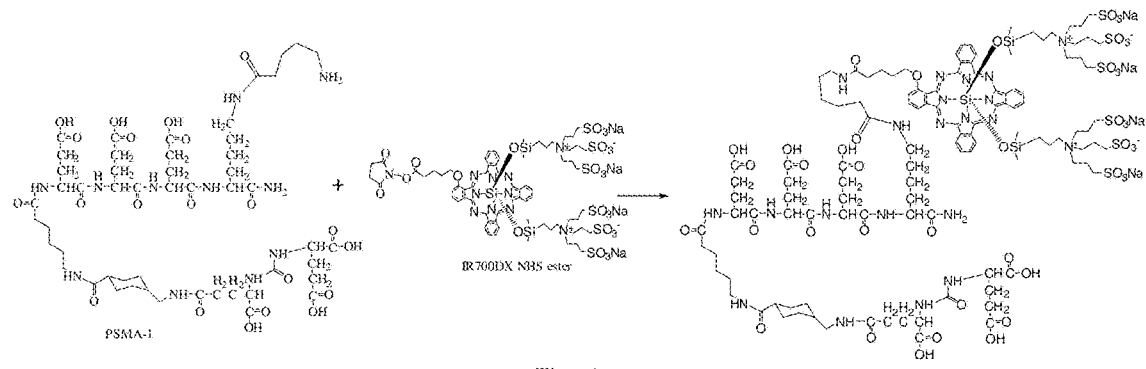
FIG. 4 illustrates a synthesis scheme for PSMA-1-IR700.

Synthesis of PSMA-1-Pc413 (FIG. 3)

Pc413 (8 mg, 0.01 mmol) was first dissolved in 1 mL of DMF, then PSMA-1-SMCC (0.007 mmol) in 100 μL of 100 mM phosphate buffer, pH 8.0 was added. The reaction mixture was stirred at room temperature for 2 hours and purified by preparative HPLC to get purified PSMA-1-Pc413. Yield: 63%. Retention time: 15.4 min. MALDI-MS: C$_{102}$H$_{134}$N$_{20}$O$_{25}$SSi$_3$, 1996.9 (found, M-C$_7$H$_{19}$NOSi); 1996.3 (calculated).

Synthesis of PSMA-1-IR700 (FIG. 4)

Coupling of PSMA-1 to IRDye700DX NHS ester (Li-Cor Biosciences) was performed in 100 mM phosphate buffer, pH 7.0. PSMA-1 (1 mg) in 200 μL of phosphate buffer was added to 0.5 mg of IRDye700DX NHS ester in 200 μL of phosphate buffer. The reaction was performed at room temperature overnight. The crude product was purified by preparative HPLC using gradient C (supplementary methods). Yield: 43%. Retention time: 28.7 min. MALDI-MS: C$_{116}$H$_{125}$N$_{21}$Na$_4$O$_{44}$S$_6$Si$_3$, 1840.9 (found, M-2 C$_{14}$H$_{30}$NNa$_2$O$_{10}$S$_3$Si); 1841.0 (calculated).

Data for PSMA-1-Pc413 and PSMA-1-IR700
In Vitro Competition Binding Results

Competition binding assay showed that both PSMA-1-Pc413 (IC$_{50}$=2.1±0.22 nM) and PSMA-1-IR700 (IC$_{50}$=2.2±0.15 nM) had binding affinities greater than 4.6-fold compared to the related ligand Cys-CO-Glu (IC$_{50}$=10.2±0.31 nM) and an affinity similar to that measured in previous studies using PSMA-1-Cy5.5 or PSMA-1-IR800.

In Vitro Uptake Results

To examine the uptake of PSMA-targeted PDT conjugates, in vitro cellular uptake of PSMA-1-PC413 and PSMA-1-IR700 in PSMA-positive PC3pip cells and PSMA-negative PC3-flu cells were performed and visualized by fluorescence microscopy. No detectable amount of fluorescence uptake was observed in PSMA-negative PC3flu cells for either PSMA-1 conjugates (FIG. 5). In contrast, for both targeted PDT agents, fluorescence intensity in PSMA-positive PC3pip cells increased with prolonged incubation time. When an excess amount of Cys-CO-Glu was included in the incubation, no fluorescence signal was observed, confirming that cellular uptake of fluorescence was attributed to the specific binding of PSMA-1-PDT conjugates to PSMA. Once internalized into PC3pip cells, the PSMA-1-PDT conjugates were located in the perinuclear position, concurring with our previous results with PSMA-NIR conjugates.

In Vitro Cytotoxicity of PDT

To determine the in vitro phototoxicity of PSMA-1-Pc413, PC3pip and PC3flu cells were incubated with PSMA-1-Pc413 at 37° C. for 1 hour and then exposed to light with radiant exposure of 0.5 J/cm$^2$. At 1 μM of PSMA-1-Pc413, 65.0±1.8% of PC3pip cells were killed, while only 22.5±3.0% PC3flu cells were killed at the same condition (P=0.0012) (FIG. 6A). When cells were treated with PSMA-1-IR700, however, no phototoxocity was observed even with prolonged incubation time (4 hours) and higher radiant exposure (up to 2.0 J/cm$^2$, FIG. 6B). We also utilized a LED diode as the light source and obtained similar results. To begin to understand the difference in PDT efficacy between the agents we measured singlet oxygen generation of the conjugates.

Singlet oxygen ($^1$O$_2$) is believed to play a key role in the efficacy of PDT. We used 1,3-diphenylisobenzofuran (DPBF) to quantify the production of singlet oxygen by each of our PDT agents by following the changes in the absorbance at 411 nm. As shown in FIG. 6C, the absorbance at 411 nm decreased quickly after PSMA-1-Pc413 or PSMA- 1-IR700 in PBS was added to DPBF solution and light irradiation was applied, suggesting high efficacy in generation of reactive $^1O_2$. When the test was performed in RPMI1640 media containing 10% FBS (FIG. 6D), the decay of DPBF resembled that in PBS for PSMA-1-Pc413; however, the decrease of absorbance at 411 nm was significantly less in RPMI media than in PBS for PSMA-1-IR700, indicating that PSMA-1-IR700 was not effective in generating singlet oxygen in RPMI media, potentially explaining the poorer in vitro cytotoxicity of PSMA-1-IR700.

In Vivo Imaging

Animals bearing both PSMA-positive PC3pip and PSMA-negative PC3flu tumors were used to demonstrate non-invasive imaging and examine the bio-distribution of PSMA-1-PDT conjugates in vivo. Selective uptake was observed in PSMA-positive PC3pip tumors. As shown in FIG. 7A, the fluorescence intensity of PSMA-1-Pc413 in PC3pip tumors increased gradually, peaking at 24 hours post-injection, and then slowly declined. The fluorescence was also observed in PC3flu tumors, but was 1.5-fold less than that in PC3pip tumors after 2 hours post-injection (P=0.029). High fluorescence was observed in the upper back of the animals at early time points, but was cleared after 24 hours post-injection; this is likely due to non-specific accumulation in the fatty region of the neck. To confirm that binding of PSMA-1-Pc413 is specific to PSMA, in vivo competition experiments were performed. When the mice were co-injected with 1 nmol of PSMA-1-Pc413 and 1000 nmol of ZJ-MCC-Ahx-YYYG, an analogue of PSMA-1 with similar binding affinity, the fluorescent intensity in PC3pip tumors decreased (FIGS. 7C-D). At 24-hour post-injection, fluorescence in PC3pip tumors decreased about 30% (P=0.0067), while no change in fluorescence intensity was observed in PC3flu tumors (P=0.345). In all cases inclusion of the unlabeled competitor ligand reduced binding in PSMA-positive PC3pip tumors to uptake levels measured in the receptor negative PC3flu tumors. Five days post-injection, mice were euthanized and tissues such as skin, liver, stomach, heart, lung, spleen, kidneys, PC3pip tumor, PC3flu tumor and bladder were taken for ex vivo imaging. PC3pip tumor showed bright fluorescent signal, while other tissues had minimal amount of fluorescence signal (FIG. 7B).

PSMA-1-IR700 showed different pharmacokinetics compared to PSMA-1-Pc413. PSMA-1-IR700 reached highest accumulation in PC3pip tumor within 30 minutes post-injection, then dropped rapidly (FIG. 8A). Compared to PSMA-1-Pc413, PSMA-1-IR700 demonstrated better selectivity. At 4-hour post-injection, the signal in PC3pip tumor (23.3±3.8 counts/s) was more than 3.6-fold higher than in PC3flu tumor (6.4±3.3 counts/s) (P=0.0018). For in vivo competition experiments, we first tried to use excess amount of ZJ-MCC-Ahx-YYYG to compete with PSMA-1-IR700 as we did with PSMA-1-Pc413; however ZJ-MCC-Ahx-YYYG failed to block the binding of PSMA-1-IR700. PSMA-1-IR700 had different pharmacokinetics from PSMA-1-Pc413, clearing very quickly from the body. To better compete for binding we tested unconjugated PSMA-1. When mice were co-injected with excess amount of PSMA-1, the signals in PC3pip tumor reduced significantly (FIG. 8C). At 4-hour post co-injection of 1 nmol of PSMA-1-IR700 and 1000 nmol of PSMA-1, the fluorescent signal in PC3pip tumor was 86% (P=0.0002) lower compared to animals received PSMA-1-IR700 only (FIG. 8D). In contrast, no significant change was observed in the signals in PC3flu tumors (P=0.065). Ex vivo tissue images showed that PSMA-1-IR700 was mainly accumulated in PC3pip tumors (FIG. 8B). Some signal was observed in the kidneys but was weaker than that in PC3pip tumors.

In Vivo Photodynamic Treatment of PC3pip Tumors

To test the photodynamic efficacy of PSMA-1-Pc413, mice bearing PC3pip tumors were irradiated with 150 J/cm$^2$ of light at 672 nm at 24-hour post-injection to take advantage of the maximum peak of PSMA-1-Pc413 tumor accumulation. Mice receiving no drug and no light were used as controls. Control groups in which mice receive light only or drug only were not included in this study since light alone or drug alone results in no PDT effect. Maestro images showed that fluorescence signal in PC3pip tumor increased when more drug was administered (FIG. 9A). Treated tumors showed immediate loss of fluorescence indicating photobleaching from the activation of Pc413 (FIG. 9B). The loss of fluorescence was also observed when mice were treated with 50 J/cm$^2$ of light. Swelling around the treated site was observed within hours after treatment. Tumor volume was significantly reduced starting on day 5 post-injection for mice receiving 0.25 mg/kg (P=0.001) or 0.50 mg/kg (P=0.0004) of PSMA-1-Pc413 when compared to untreated controls (FIG. 9C). As the drug dose increased, improved treatment efficacy was observed. The increased drug accumulation in the tumor, therefore, likely led to better treatment results. At the dose of 0.25 mg/kg and 0.5 mg/kg, tissue damage was observed in some animals due to tumor damage/necrosis; no other adverse effects were observed.

For mice treated with PSMA-1-IR700, we first tried to treat the animals at 2-hour and 4-hour post-injection to allow the conjugate to distribute in the tumor and clear from the body; however, no PDT effect was observed. We then moved the treatment time to 1-hour post-injection to maximize tumor associated drug at the time of irradiation. In order to improve the treatment outcome, mice received PSMA-1-IR700 on days 0, 4 and 8 and were treated with light at 1-hour post-injection. Similar to PSMA-1-Pc413, fluorescence signal in PC3pip tumors was dose-dependent (FIG. 9D). Fluorescence signal in PC3pip tumors disappeared after irradiation to light (FIG. 9E). The loss of fluorescence was also observed at a lower dose of 30 J/cm$^2$ light. Significant tumor growth inhibition was observed starting on day 7 post PDT treatment. Compared to untreated control mice, tumor sizes in mice exposed to PDT treatments were significantly reduced. The PDT effect of PSMA-1-IR700 was dose-dependent (FIG. 9F). Treatment did not affect physical appearance and activity of the mice; no overt toxicity was observed.

For histological analysis, tumors were extracted 24 hours after single PDT treatment with PSMA-1-PDT. Tissues were processed using hematoxylin and eosin staining. Pathological analysis showed dramatic differences between the treated and untreated tumors (FIG. 10). Nuclei in cancer cells treated with PSMA-1-PDT conjugates were much smaller compared to untreated tumors, indicating that the cells were damaged; in contrast the untreated tumor was not damaged and the cells were intact.

Our rationally designed dual-functional PSMA-1-PDT conjugates have potential to serve as anti-cancer agents and to our knowledge represent the first PSMA-targeted PDT agents. Through in vitro and in vivo studies, we have demonstrated that there are differences in the PDT efficacy of each of the two targeted agents that are likely related to the PDT moiety and not the targeting ligand, as the affinity remains unchanged after conjugation to either of the PDT agents. The effectiveness and features of our PSMA-1-Pc413 conjugate suggest that it has potential clinical utility and may represent a next-generation theranostic PDT agent. The dual use of the developed PSMA-1-Pc413 conjugate may offer surgeons photoablation as an adjunct to surgical resection to spare proximate nerves and muscles and eliminate stray cancer tissue and cells, potentially reducing the frequency of unresected tumor and cancer recurrence.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A phthalocyanine compound or targeted conjugate thereof having the formula (I):

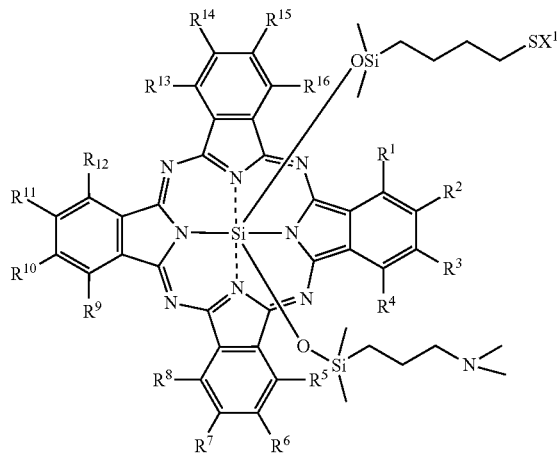

wherein $X^1$ is hydrogen or includes a targeting moiety directly or indirectly coupled or conjugated to the thiol group;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

2. The phthalocyanine compound or targeted conjugate thereof of claim 1, wherein $R^1$-$R^{16}$ are independently selected from the group consisting of hydrogen, halogen, nitro, cyano, hydroxyl, thiol, amino, and methyl.

3. The phthalocyanine compound or targeted conjugate thereof of claim 1, having the formula (II):

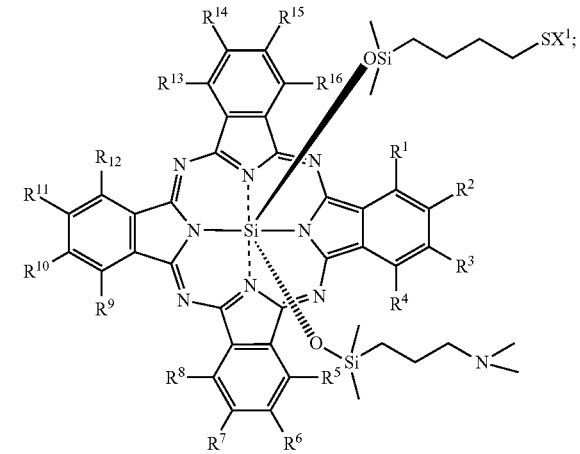

wherein $X^1$ is hydrogen or includes a targeting moiety directly or indirectly coupled or conjugated to the thiol group;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

4. The phthalocyanine compound or targeted conjugate thereof of claim 3, wherein $R^1$-$R^{16}$ are independently selected from the group consisting of hydrogen, halogen, nitro, cyano, hydroxyl, thiol, amino, and methyl.

5. The phthalocyanine compound or targeted conjugate thereof of claim 1 having the formula (III):

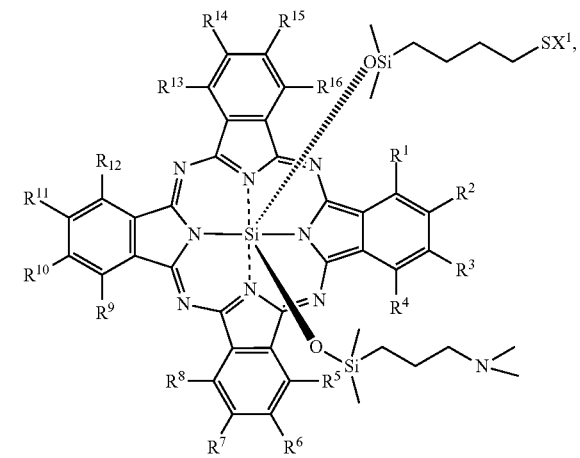

wherein $X^1$ is hydrogen or includes a targeting moiety directly or indirectly coupled or conjugated to the thiol group;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

6. The phthalocyanine compound or targeted conjugate thereof of claim 5, wherein $R^1$-$R^{16}$ are independently selected from the group consisting of hydrogen, halogen, nitro, cyano, hydroxyl, thiol, amino, and methyl.

7. The phthalocyanine compound or targeted conjugate thereof of claim 1, having the formula (IV):

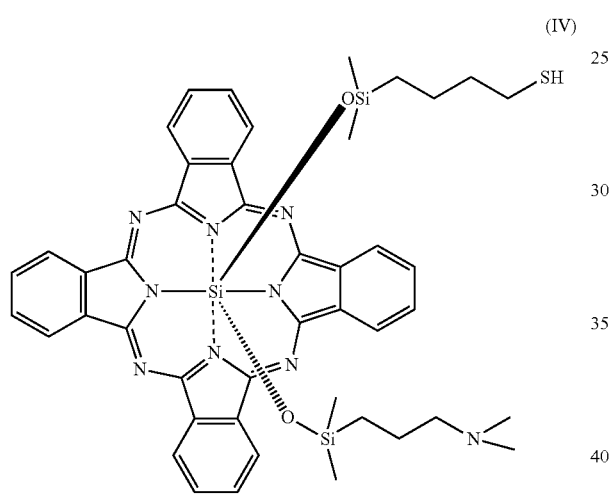

(IV)

and pharmaceutically acceptable salts thereof.

8. The phthalocyanine compound or targeted conjugate thereof of claim 1, wherein the phthalocyanine compound is coupled or conjugated to a targeting moiety.

9. The phthalocyanine compound or targeted conjugate thereof of claim 8, wherein the targeting moiety is selected from the group consisting of a polypeptide, polynucleotide, small molecule, elemental compound, antibody, and antibody fragments.

10. The phthalocyanine compound or targeted conjugate thereof of claim 8, wherein the phthalocyanine compound is directly coupled or conjugated to a targeting moiety.

11. The phthalocyanine compound or targeted conjugate thereof of claim 8, wherein the phthalocyanine compound is coupled or conjugated to a targeting moiety via a linker.

12. The phthalocyanine compound or targeted conjugate thereof of claim 8, wherein the targeting moiety is coupled or conjugated to the thiol group of the phthalocyanine compound.

13. The phthalocyanine compound of or targeted conjugate thereof of claim 8, the targeting moiety comprising a prostate specific membrane antigen (PSMA) ligand.

14. The phthalocyanine compound or targeted conjugate thereof of claim 13, the PSMA ligand comprising a PSMA-1 ligand.

15. A pharmaceutical composition comprising a phthalocyanine compound or targeted conjugate thereof having the formula (I):

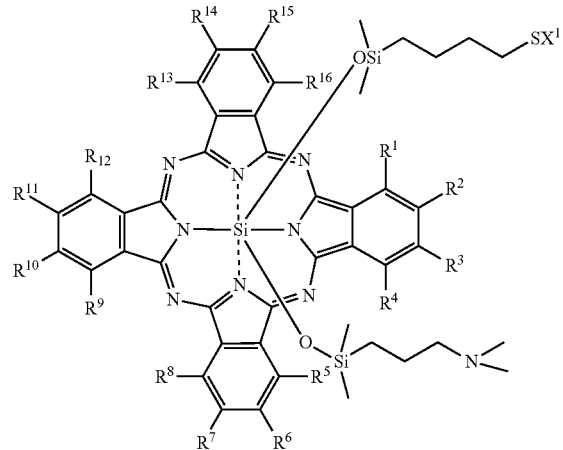

wherein $X^1$ is hydrogen or includes a targeting moiety directly or indirectly coupled or conjugated to the thiol group;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

16. The pharmaceutical composition of claim 15, wherein $R^1$-$R^{16}$ are independently selected from the group consisting of hydrogen, halogen, nitro, cyano, hydroxyl, thiol, amino, and methyl.

17. The pharmaceutical composition of claim 15, having the formula (II):

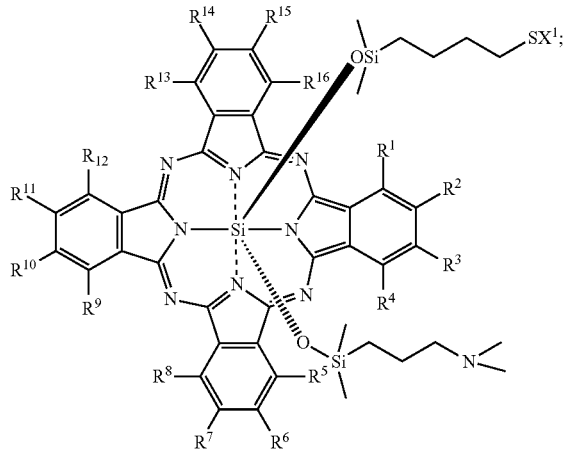

wherein $X^1$ is hydrogen or includes a targeting moiety directly or indirectly coupled or conjugated to the thiol group;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$ $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

18. The pharmaceutical composition of claim 17, wherein $R^1$-$R^{16}$ are independently selected from the group consisting of hydrogen, halogen, nitro, cyano, hydroxyl, thiol, amino, and methyl.

19. The pharmaceutical composition of claim 15, having the formula (III):

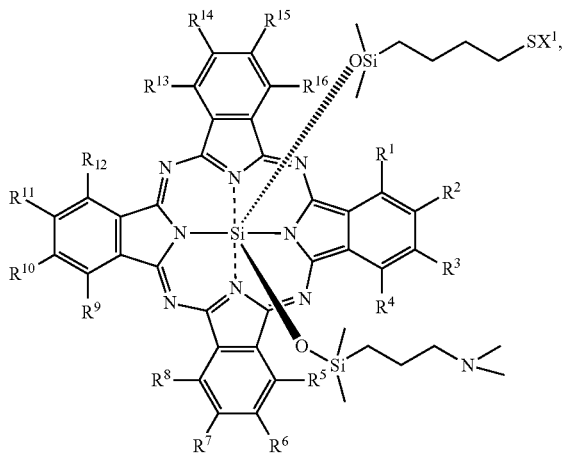

wherein $X^1$ is hydrogen or includes a targeting moiety directly or indirectly coupled or conjugated to the thiol group;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$,$R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

20. The pharmaceutical composition of claim 15, wherein $R^1$-$R^{16}$ are independently selected from the group consisting of hydrogen, halogen, nitro, cyano, hydroxyl, thiol, amino, and methyl.

21. The pharmaceutical composition of claim 15, having the formula (IV):

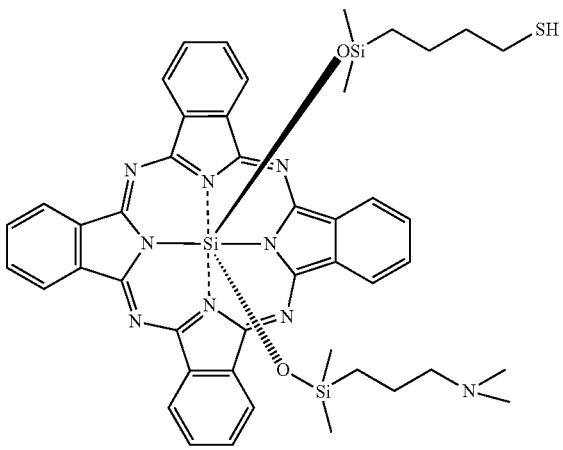

and pharmaceutically acceptable salts thereof.

22. The pharmaceutical composition of claim 15, wherein the phthalocyanine compound is coupled or conjugated to a targeting moiety.

23. The pharmaceutical composition of claim 22, wherein the targeting moiety is selected from the group consisting of a polypeptide, polynucleotide, small molecule, elemental compound, antibody, and antibody fragments.

24. The pharmaceutical composition of claim 22, wherein the phthalocyanine compound is directly coupled or conjugated to a targeting moiety.

25. The pharmaceutical composition of claim 22, wherein the phthalocyanine compound is coupled or conjugated to a targeting moiety via a linker.

26. The pharmaceutical composition of claim 22, wherein the targeting moiety is coupled or conjugated to the thiol group of the phthalocyanine compound.

27. The pharmaceutical composition of claim 22, the targeting moiety comprising a prostate specific membrane antigen (PSMA) ligand.

28. The pharmaceutical composition of claim 27, the PSMA ligand comprising a PSMA-1 ligand.

29. The pharmaceutical composition of claim 15, the composition formulated for systemic administration.

* * * * *